United States Statutory Invention Registration [19]

[11] Reg. Number: H272

Gilbert [43] Published: May 5, 1987

[54] POLY(ALLYL AZIDO NITRATES)

[75] Inventor: Everett E. Gilbert, Morristown, N.J.

[73] Assignee: The United States of America as represented by the Secretary of the Army, Washington, D.C.

[21] Appl. No.: 845,669

[22] Filed: Mar. 26, 1986

[51] Int. Cl.[4] ..... C07C 117/00; C08F 26/06; C08F 226/06

[52] U.S. Cl. ..... 525/328.8; 260/349; 526/258; 526/310; 149/19.91

*Primary Examiner*—Edward A. Miller
*Assistant Examiner*—Jack Thomas
*Attorney, Agent, or Firm*—Anthony T. Lane; Harold H. Card, Jr.; Edward F. Costigan

[57] ABSTRACT

Novel poly (allyl azide) compositions are produced by reacting a poly (allyl nitrate) of molecular weight at least about 400 with a metal azide in the presence of an inert liquid solvent or diluent. The poly (allyl azides), which may contain residual nitro groups, are energetic materials, which are useful in propellants for guns, missiles and rockets and in detonator and igniter compositions for explosive charges.

1 Claim, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

POLY(ALLYL AZIDO NITRATES)

GOVERNMENTAL INTEREST

The invention described herein may be manufactured, used and licensed by or for the Government for Governmental purposes without payment to me of any royalties thereon.

BACKGROUND OF THE INVENTION

In the past azidonitrate polymers have been prepared by copolymerizing azido monomers and nitrate monomers, which is a relatively costly and cumbersome procedure. U.S. patent application Ser. No. 600,869, filed Apr. 16, 1984, pending, Everett E. Gilbert, inventor, describes the preparation of novel polyvinyl azido nitrates by reaction of poly (vinyl nitrates) with metal azides. The poly(vinyl azides) and azido nitrates thus obtained are energetic compositions useful in propellants, detonators, etc. U.S. Pat. No. 3,654,917, E. J. Vanderberg, discloses linear poly (glycidyl azides) obtained by reacting a homo or copolymer of epichlorohydrin with a metal azide. Known polymeric azides, such as the glycidyl azide polymers of the patent, are less energetic and more costly than the poly (vinyl azides) of the aforesaid patent application.

SUMMARY AND DETAILED DESCRIPTION OF THE INVENTION

The present invention relates to a novel class of poly (allyl azide) compositions and to a process for producing the same.

The novel poly (allyl azide) compositions of this invention are essentially linear allyl polymers having a molecular weight of at least about 300, wherein from about 1% to 100% of the repeating units are allyl azide monomer units of the formula $$-CH_2-\underset{\displaystyle CH_2N_3}{\underset{|}{CH}}-$$

and from about 0% to 99% of the repeating units are allyl nitrate monomer units of the formula $$-CH_2-\underset{\displaystyle CH_2ONO_2}{\underset{|}{CH}}-$$

The poly (allyl azide) compositions of this invention are energetic materials useful in gun, missile and rocket propellants and other purposes such as in detonation and igniter compositions for explosive charges.

The allyl polymers of this invention contain the azide and nitrate groups attached to primary carbon atoms, viz. $-CH_2N_3$ and $-CH_2ONO_2$ respectively, whereas the poly (vinyl azide/nitrate) compounds of the aforesaid patent application contain the said groups attached to secondary carbon atoms, viz. $-CHN_3$ and $-CHONO_2$ respectively. The poly (allyl azide/nitrate) products of this invention are preferred, since the primary type of group is somewhat more chemically stable than the secondary type of group.

The allyl azide polymers of the present invention can be prepared by reacting a poly(allyl nitrate) of molecular weight at least about 400 with a metal azide, preferably in the presence of a liquid solvent or diluent inert to the reaction. The chemical reaction involved therein can be represented essentially as follows:

$$-(CH_2CH(CH_2ONO_2))_x- \xrightarrow{MeN_3} -[CH_2CH(CH_2ONO_2)]_a- [CH_2CH(CH_2N_3)]_b-$$

wherein X = a + b.

The reaction can be carried out at a temperature of from about 20° C. to 125° C. and preferably from about 50° C. to 100° C. The reaction time, temperature, and amount of metal azide can be varied widely depending on the desired degree of replacement of the nitro groups in the poly (allyl nitrate). For example, the reaction time can vary from less than an hour to many hours and the amount of metal azide can vary from about 100% to about 200% of the stoichiometric amount required to react with the nitro groups of the poly (allyl nitrate).

Liquid solvents or diluents which are suitable for use in the process of the present invention include dimethylformamide, dimethylsulfoxide, tetrahydrofuran, acetonitrile, hexamethylphosphoramide and water and 1-methyl-2 -pyrolidinone, acetone, and 2-methoxyethanol. The reaction is preferably carried out in a solvent in which at least one of the reactants (metal azide and polyallyl nitrate) is soluble.

Alkali metal azides, such as sodium, lithium and potassium azides, are preferably utilized for carrying out the present reaction, but any stable metal azide, particularly an alkaline earth metal azide, e.g. calcium azide, can be employed in a similar manner.

The following examples illustrate the invention.

Example 1

Poly (allyl nitrate) (0.6 g), sodium azide (0.6 g) and dimethylformamide (25 ml) were mixed and heated with agitation for 5 hours at 80° C. The reaction mixture was poured into about 100 ml. water and acidified with hydrochloric acid to precipitate the product as a gum. The precipitate was separated by filtration and dried under a heat lamp, yielding 0.35 g. of material, whose infrared spectrum showed the strong azide peak 2100 $cm^{-1}$ and weak peaks for nitrate 1620, 1280 and 860 $cm^{-1}$.

Match Test. A small quantity of the product thus obtained, when heated on a spatula over a low Bunsen flame, produced a strong flash, showing the highly energetic nature of the material.

The poly (allyl nitrate) employed in this example was prepared by nitration of poly(allyl alcohol) as described below. (General references to this preparation are given in Dutch Patent No. 66,784 (1950) per Chem. Abstracts 45,5452 (1951) and by Schulz et al. (Makromol. Chem. 67,192 (1963)).

0.5 g Poly (allyl alcohol) (no. ave. mol. wt. 4000; wt. ave. mol. wt. 20,000; hydroxyl value 30%; analysis: Theory C, 62.0; H, 10.4; found: C, 62.9; H, 10.5; ash 1%; Cl, 0.4%; Zn 0.12%) was added to a mixture of 10 ml. 100% nitric acid and 20 ml. methylene chloride with agitation at 5° C. The reaction mixture was stirred for 30 minutes at 5° C. and then drowned in ice water, whereupon the product separated as a viscous grease. The product was dissolved in acetone and the solution was evaporated in dryness, yielding 0.8 g. (78%) of poly (allyl nitrate) product, a clear yellow, viscous semisolid, which gave a positive match test. The IR spectrum of the material showed peaks for the nitrate group at 1620, 1280 and 860 $cm^{-1}$, and the absence of the hydroxyl peak at 3400 $cm^{-1}$ which was present in the starting compound.

Example 2

The procedure of Example 1 was repeated except that the reaction mixture was heated for 19 hours instead of 5 hours. The product weighed 0.4 g. and its infrared spectrum showed the strong azide peak and weak nitrate peaks. It analyzed 42.4% nitrogen, which corresponds to a ratio of 2 allyl nitrate monomer units to 9 allyl azide monomer units in the polymer (values of 2 and 9 for a and b respectively in the foregoing formula). The product gave an energetic match test.

Example 3

Poly(allyl alcohol) was prepared according to the method of Kargin et al., Ger. Offen. 1,907,612 (Chem. Abstracts 74,142661) by Cobalt 60 polymerization of allyl alcohol (30.1 g.) mixed with calcium chloride (32.5 g.) and water (48 ml.) using $9\times10^4$ rad/hr for 236 hours (21.2 megarads total). The resulting solution was processed by treatment with methanolic potassium hydroxide followed by thorough extraction of the precipitated $Ca(OH)_2$ with hot methanol. Evaporation to dryness yielded 22.0 g. (73% yield) of polyallyl alcohol.

The poly (allyl alcohol) was nitrated by the procedure described in Example 1 and yielded a product which possessed an IR spectrum identical with that of the polyallyl nitrate material described in Example 1.

The poly (allyl nitrate) thus obtained (1.6 g.) was reacted with sodium azide (1.6 g.) in dimethylformamide (40 ml.) at 75°-85° C. for 6 hours and the reaction mixture was worked up as described in Example 1. The product weighed 1.2 g. and was a viscous brown oil, which gave a positive match test and an IR curve showing strong azide absorption and residual nitrate groups.

Example 4

Poly (allyl alcohol) was prepared by heating allyl alcohol in the presence of hydrogen perioxide as described in Example 9 of U.S. Pat. No. 2,541,155. The poly (allyl alcohol) thus obtained (mol. wt. about 280) was nitrated by the method described in Example 1 above. The IR spectrum of the resulting product showed the presence of nitrate groups and the absence of hydroxyl groups. Analysis: Calculated for $C_3H_5NO_3$: C, 35.0; H, 4.9; found: C, 34.7; H, 4.5.

The poly(allyl nitrate) thus obtained (1.8 g.) was reacted with sodium azide (2.0 g.) in dimethylformamide (50 ml.) at 75°-85° C. for 6 hours by the method described in Example 1. The product (1.1 g.) gave an IR spectrum showing the presence of azide and nitrate groups, and produced a positive match test.

I claim:

1. An essentially linear allyl azide polymer having a molecular weight of at least about 300, wherein from about 1% to 100% of the repeating units are allyl azide monomer units of the formula $$-CH_2-\underset{\displaystyle CH_2N_3}{\underset{|}{CH}}-$$

and from 0% to about 99% of the repeating units are allyl nitrate monomer units of the formula $$-CH_2-\underset{\displaystyle CH_2ONO_2}{\underset{|}{CH}}-$$

* * * * *